United States Patent
Zakharov et al.

(10) Patent No.: US 12,336,758 B2
(45) Date of Patent: Jun. 24, 2025

(54) DEVICE AND METHOD FOR MAPPING OF VISUAL SCENE ONTO PROJECTION SURFACE

(71) Applicant: Vivior AG, Zurich (CH)

(72) Inventors: Pavel Zakharov, Volketswil (CH); Michael Mrochen, Zug (CH)

(73) Assignee: Carl Zeiss Vision International GmbH, Aalen (DE)

(*) Notice: Subject to any disclaimer, the term of this patent is extended or adjusted under 35 U.S.C. 154(b) by 606 days.

(21) Appl. No.: 17/637,170

(22) PCT Filed: Jul. 30, 2020

(86) PCT No.: PCT/EP2020/071539
§ 371 (c)(1),
(2) Date: Feb. 22, 2022

(87) PCT Pub. No.: WO2021/043512
PCT Pub. Date: Mar. 11, 2021

(65) Prior Publication Data
US 2022/0280035 A1 Sep. 8, 2022

(30) Foreign Application Priority Data
Sep. 5, 2019 (EP) ..................... 19195656

(51) Int. Cl.
*A61B 3/024* (2006.01)
*A61B 3/113* (2006.01)
*G06F 3/01* (2006.01)

(52) U.S. Cl.
CPC .............. *A61B 3/024* (2013.01); *A61B 3/113* (2013.01); *G06F 3/012* (2013.01)

(58) Field of Classification Search
CPC ......... A61B 3/024; A61B 3/113; G06F 3/012; G02C 7/061; G02C 7/027; G02C 13/005
(Continued)

(56) References Cited

U.S. PATENT DOCUMENTS

2007/0229761 A1 10/2007 Carol et al.
2017/0090220 A1 3/2017 Bonnin et al.
(Continued)

FOREIGN PATENT DOCUMENTS

CN 107333121 11/2017
CN 109923499 11/2017
(Continued)

OTHER PUBLICATIONS

China National Intellectual Property Administration, CN Examination Report for International Patent Application No. 202080076179.2, Jun. 28, 2023.
(Continued)

*Primary Examiner* — Wyatt A Stoffa
*Assistant Examiner* — Rahman Abdur
(74) *Attorney, Agent, or Firm* — Williams Mullen; Thomas F. Bergert

(57) ABSTRACT

Embodiments disclosed herein determine an optical parameter distribution at a projection surface. Embodiments of the system disclosed herein comprise a visual field sensor and a head orientation and/or position sensor. The visual field sensor is configured to measure a visual field of a user related to a specific vision task in a visual field of a user. The head orientation and/or position sensor is configured to measure head orientation and/or position of the user in relation to the visual field during the specific vision task. The system is configured to enable computation of the user's eye orientation in relation to the head of the user based on the gaze directions of the user and the head orientation and/or position of the user to determine an optical parameter distribution at a projection surface between the visual field and a retina of the user.

15 Claims, 8 Drawing Sheets

Figure 1:
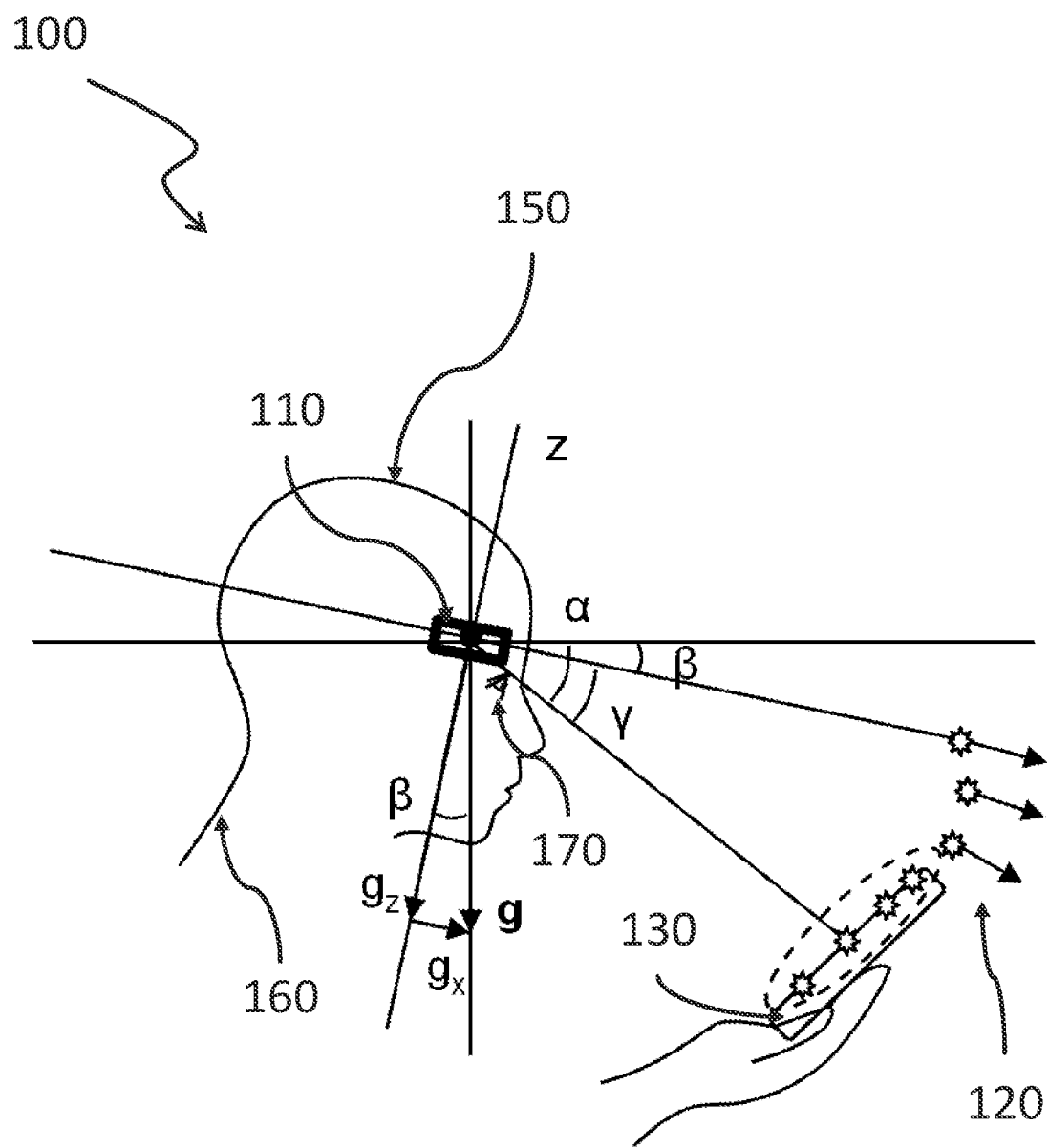

(58) Field of Classification Search
USPC .......................................................... 351/224
See application file for complete search history.

(56) References Cited

U.S. PATENT DOCUMENTS

| | | |
|---|---|---|
| 2019/0113770 A1 | 4/2019 | Tranvouez-Bernardin et al. |
| 2019/0142268 A1 | 5/2019 | Zakharov et al. |

FOREIGN PATENT DOCUMENTS

| | | |
|---|---|---|
| CN | 109068972 | 12/2018 |
| EP | 3508882 | 7/2019 |
| JP | 2007536043 | 12/2007 |
| JP | 2012066002 | 4/2012 |
| JP | 2019513519 | 5/2019 |
| WO | 2017042824 | 3/2017 |

OTHER PUBLICATIONS

European Patent Office, EP Examination Report for Application No. 19 195 656.4, Jun. 16, 2023.
Israel Patent Office, Israel Examination Report for International Patent Application No. IL 290662, Jun. 30, 2024.
Japanese Patent Office, JP Examination Report for International Patent Application No. 2022-514721, Apr. 9, 2024.
International Search Report and Written Opinion for PCT/EP2020/071539, European Patent Office, Nov. 11, 2020.
Search Report for European Application No. 19195656.4, European Patent Office, Mar. 4, 2020.
Japanese Patent Office, JP Examination Report for International Patent Application No. 2022-514721, Dec. 3, 2024.
Korean Intellectual Property Office, Korean Examination Report, International Patent Application No. KR 10-2022-7007382, Jan. 21, 2025.

DEVICE AND METHOD FOR MAPPING OF VISUAL SCENE ONTO PROJECTION SURFACE

CROSS-REFERENCE TO RELATED APPLICATIONS

This application is the U.S. national phase of international application PCT/EP2020/071539, filed on Jul. 30, 2020, which claims the benefit of European application EP 19195656.4 filed on Sep. 5, 2019; all of which are hereby incorporated herein in their entirety by reference.

Examples relate to concepts for customizing optical aids and applications thereof and in particular to a system and method for determining an optical parameter distribution at a projection surface.

Presbyopia is a condition developed with the natural aging of the eye which manifests itself as a worsening ability to accommodate the lens of the eye. The typical onset is above 35 years and this condition develops progressively until complete cessation of accommodation abilities. Multiple solutions have been developed through human history with significant progress achieved in the recent decades. The most common remedy is reading eyeglasses, which are used for near tasks. The reading eyeglasses artificially extend the accommodation range of the eye. A user requiring vision correction for far vision as well (e.g. due to myopia) is required to wear at least two pairs of spectacles and change them based on the required task. This may be inconvenient.

Thus, the user may use glasses having multiple optical powers. This can be achieved by geometrically separating zones of different optical power, such as in bifocal and trifocal glasses. The user of such glasses has an option to select the required optical power by looking on the object of interest through a required zone. The positions of the respective zones are selected based on a natural correlation of tasks and eye angles: the higher power is typically located in the lower zone (near zone), since the near vision tasks are typically performed by aligning the object in the lower gaze zone (such as reading, smartphones, etc.). The upper zone is thereby reserved for the far vision tasks (far zone). In trifocal glasses, an intermediate zone exists between near and far zones to support vision in middle range. Further to that, progressive addition lenses exist which do not have visible lines separating respective optical power zones and instead have smooth transitions from one zone to another.

Since such a spatially separated corrective solution is neither natural nor intuitive for human eyes, the user must adapt thereto. Special consideration takes fitting the zones to the requirements of the particular user in order to minimize possible disruption of the user's viewing habits developed through lifespan. Thus, preferably a corrective solution has to be adapted to the individual visual behaviour. Such customization could include optimal mapping of optical powers and/or other optical parameters to the surface of an optical aid, such as spectacles. The terms customization, individualization and personalization are further used interchangeably. The optical aid may also be called vision aid or visual aid herein. The optical aid may be an additional/enhancing optical element to the natural visual system of an eye, such as spectacles, contact lenses, augmented or virtual reality headsets, retinal or other visual implants, corneal inlays, etc. The optical aid may be a replacement of the natural element of the visual system, such as intraocular lens as a replacement of the natural lens. The optical aid may be a modification of the element of the visual system, such as refractive surgery performed on the cornea or on the lens. The optical aid may be a combination of forms of optical aids.

Understanding of lens position in the finished optical aid in relation to the user's eyes is important, if not essential for customization. Further to that, understanding the user's visual behavior is important, if not essential. This includes how the user typically positions objects (related to specific vision tasks) in his/her visual field and how the user positions his/her body, head and eyes in relation to the objects related to the specific vision tasks.

An exemplary vision task is reading. A handheld media (for example book or electronic device) is typically positioned in such a way that the head is inclined roughly half-way to the object, while the remaining required inclination angle is adjusted by the eyes themselves. The difference between the head's inclination angle and the eyes' inclination angle is individual as well as the positioning of the media in the visual field.

It is thus critically important to understand the preferred angle between the user's gaze/eyes/head in order to better customize a distribution of visual zones at the optical aid.

Optical aids may have to be optimized with respect to user-specific preferences.

Such a demand may be satisfied by the subject-matter of the claims.

According to a first aspect, a system for determining an optical parameter distribution at a projection surface is provided. The system comprises a visual field sensor. The visual field sensor is configured to measure a visual filed of a user related to a specific vision task, for example identify an object related to the specific vision task in the visual field of the user. The visual field sensor is further configured to determine gaze directions of the user during the specific vision task. The system comprises a head orientation and/or position sensor. The head orientation and/or position sensor is configured to measure head orientation and/or position of the user in relation to the visual field during the specific vision task. The system is configured to enable computation of the user's eye orientation in relation to the head of the user based on the gaze directions of the user and the head orientation and/or position of the user to determine an optical parameter distribution at a projection surface between the visual field and a retina of the user.

An optical parameter may be a distance to an object related to the vision task, which may be mathematically linked to the optical power of the optical aid. The optical parameter may be a luminance of the object of the vision task, which may be linked to the pupil size of the eye during the specific vision task. The optical parameter may be a spectral content of light originating from the object related to the vision task. The optical parameter may include an angular distribution of light field detected from the visual field. The optical parameter may include a polarization state and polarization degree of light detected from the visual field.

Thus, instead of direct monitoring of the eyes' movements of the user and viewing directions for a specific vision task, the eyes' movements of the user with respect to the head movements can be calculated from the head and gaze angles. Directly monitoring the eyes' movements needs to be performed in familiar settings of an everyday routine of the user and may need sufficient statistics to be accumulated in long-term continuous measurements in order to obtain reliable estimates. However, long term monitoring of the eyes' movements of the user can be disadvantageous due to the cumbersomeness of the existing eye-tracking solutions, alignment requirements and battery consumption of the equipment. This can be avoided by a system according to the first aspect.

The visual field sensor may be configured to measure at least one parameter of the visual field. The parameter of the visual field may be measured with at least a single dimensionality. For example, the parameter may be resolved in a polar coordinate system along at least one angle of rotation, such as pitch (inclination, rotation around horizontal axis of the sensor), yaw (rotation around vertical axis) or roll (rotation around transverse axis) angles. Additionally or alternatively, the parameter of the visual field, i.e. the visual field parameter, can be resolved in a cartesian coordinate system along the position coordinates.

Additionally or alternatively, the visual field sensor may be configured to measure the visual field parameter in two or three dimensions. The parameter of the visual field may be at least one of the following: distance to the objects of the visual field; intensity, spectral properties, polarization parameters (e.g. degree of polarization, Stokes parameters) and/or light-field parameters of light emitted and/or reflected by objects of the visual field.

The visual field sensor may be further configured to enable determination of gaze direction. This can be achieved in multiple ways. In one simple example, the visual field sensor may comprise or be a directional sensor mounted on the spectacles and directed forwards and coaligned with the optic/optical axis of spectacles. The directional light sensor may be based on optics or be light based. The directional sensor may also be any kind of directional distance sensor, for example RADAR or LIDAR. The directional sensor may be capable of moving together with the spectacles. The system may also comprise the head orientation sensor aligned with the spectacles or other device, the system can be mounted on. Due to the natural head movements of the user, the directional sensor may be capable of sampling an environment in different directions; in combination with the head orientation sensor, the system may allow obtaining an angle-resolved image of lightning conditions.

When the user is reading content on a handheld electronic device with an illuminated screen (e.g. smartphone or a tablet), the directional sensor may be configured to detect the light emitted by the device. Due to head dynamics, the directional sensor may be configured to occasionally detect light emitted from the device.

Corresponding inclination angles $\alpha$ indicate the gaze directions. At the same time, during reading activity, a head orientation, for example the head pitch angle, may in average equal $\beta$. Angle $\beta$ may be typically lower in absolute value than the gaze angles $\alpha$. The eye angle can be found as $\alpha$-$\beta$. In this way, knowing the type of vision activity, object of vision activity may allow estimating the eye angle from gaze and head orientation.

The visual field sensor may use the directional sensor, also coaligned with the optic/optical axis of spectacles. Due to the natural head movements in combination with measurements of the head/device orientation sensor, a map of distances to the surrounding objects can be constructed. This can also be performed by the processing unit, as introduced below. By knowing a priory the type of vision task, the user can identify the handheld device as an object located in a vicinity of the user (for example by a user input). Further analysis may be performed in a way similar to the example above.

The directional sensor may be tilted downwards in relation to the optical axis of spectacles in order to collect more measurements from the handheld media. For example, for a typical gaze inclination during reading of handheld media of 30°, it is advantageous to tilt the directional visual field sensor downwards by the same angle in order to increase the sampling density from the object of vision activity (handheld media or device) in the typical case. This may be achieved by permanently directing the visual field sensor downwards. Alternatively or additionally, the system may comprise at least two directional sensors, at least one of which may be directed downwards by a required angle. The system may be configured to enable or disable directional sensors based on the identified vision activity.

Alternatively or additionally, the system may be configured to change the direction of the visual field sensor in order to optimise the density of data based on the visual activity/task performed by the user. In one implementation, the visual field sensor may be configured to use a scanner to sample the parameter of the visual field in different directions. Based on the identified activity, the density of sampling may be adjusted to obtain more samples of the object of interest such as object of vision activity.

The specific vision task may be understood as the activity related to vision which is characterized by the relative consistency of the visual field, for example reading, writing, driving, using handheld devices or watching TV. The vision task may also be selected beforehand, while performing the task or later.

The system may be configured to perform measurements of a single activity, such as reading. In this case the object, acquired by the visual field sensor, may be known a priory as reading media/material (such as book or handheld device) and thus the majority of the sensor measurements are related to the reading material. In this example, processing of the data can be performed with simple statistical methods meant to discard outliers, in particular, robust statistical processing. In a similar fashion, the measurements of the head orientation sensor may correspond to the head orientation of reading activity and thus processing can be performed with a method of reduced complexity, such as simple statistical methods.

The system may comprise a user input which may enable the user to indicate the vision task and/or the object related to the vision task. The user input may be implemented on the device itself or on an accompanying computing device, such as a mobile phone or a mobile computer. Further, the user input may be implemented on a cloud interface.

The visual field sensor may be configured to identify an object of the visual field of the user related to the specific vision task. Further, the visual field sensor may be configured to derive the gaze directions of the user related to the identified object of the visual field.

The system may further comprise a context sensor. The context sensor may be configured to measure at least one parameter related to an activity of the user.

The system may further comprise a statistical classifier. The statistical classifier may be part of the processing unit as described below. The statistical classifier may be configured to identify the vision task and/or object of the visual field of the user from at least one of the visual field sensor, the head orientation and/or position sensor, and the context sensor. Identification may be at least in part performed automatically, for example with methods of statistical analysis/modelling.

The context sensor may be adapted to measure at least one context parameter related to the vision task of the user. The context sensor may be adapted to enable the system to derive statistical characteristics of the measured context parameter to be compared with statistical characteristics of a signature context parameter associated with specific vision tasks. These statistical characteristics of the measured context parameter may be stored on or in a memory unit. The memory unit may also include the signature statistical characteristics of the context parameter (stored beforehand).

The system may further comprise a memory unit such as the aforementioned memory unit. The memory unit may be configured to store the head orientation and/or position, in particular head angles, and the gaze directions, in particular gaze angles, both related to the specific vision task. The head angles and the gaze angles may be stored during the time of performing the specific vision task. The stored head orientation and/or position, in particular the stored head angles, and the stored gaze directions, in particular gaze angles, may form the basis for determining the optical parameter distribution at the projection surface between the visual field and the retina of the user.

In consequence, the information about the optical parameter distribution may be stored for later customization of an optical aid for the user.

The system may further comprise a processing unit. The processing unit may be configured to determine the corresponding differences between the head orientation and/or position, in particular head angles, and the gaze directions, in particular gaze angles, and to determine the optical parameter distribution at the projection surface between the visual field and the retina of the user.

The processing unit may be configured to determine the corresponding differences between the stored head orientation and/or position, in particular head angles, and the stored the gaze directions, in particular gaze angles, and to determine the optical parameter distribution at the projection surface between the visual field and the retina of the user.

In consequence, the optical aid for the user can be customized straight away after simple use of the system.

The processing unit may be connected to the memory unit. Further, the memory unit may be interleaved such that the processing unit may comprise its own integrated memory. Computation may then be performed on the processing unit promptly or after a measurement session has been performed by the user. Thus, the user may be provided with prompt adaptation/customization of his/her optical aid or the results may be stored for the option to gather data for longer assessing the user in order to provide optimal customization of the optical aid.

These signature statistical characteristics associated with the context parameter may be fed to the memory unit beforehand, during or after measuring the context parameter. The memory unit and the context sensor may thus be in direct communication with each other. This also applies to the processing unit which may perform the correlation/comparison of the respective statistical characteristics.

The context parameter may be a metric of motion of the user, for example, motion intensity, amount of acceleration, direction of acceleration, amount and/or direction of rotation. The context parameter may also be an illumination condition, such as light intensity, direction and spectral content, presence of flickering and it's frequency. The context parameter may be a location and orientation of the user, estimated with location and positioning methods, such as global and local positioning systems, wireless signal quality, etc. The context sensor may include an imaging system configured to obtain images of the visual field as well as surrounding of the user and/or user himself/herself.

The context sensor can be a wearable camera. Alternatively or additionally, the camera is mounted outside of the users' body. For example, the camera may be a camera of a device, like mobile phone, handheld computer, tablets, laptop and desktop computer, or can be a separate camera module placed on the desktop.

The context sensor may be a microphone configured to measure acoustic vibrations (sound) around user. Intensity, spectral content and pattern may be used as context parameters. The context sensor may be equipped with the detector of electromagnetic radiation in radio frequency range to enable detection of signals from wireless radio emitters. For example, the radio waves of GSM, GPS, WiFi, Bluetooth can be used.

Additionally or alternatively, the system may be configured to detect signals of wireless emitters. The system may be equipped with an electromagnetic receiver configured to receive signals. Such signals may be communicated by means of electromagnetic waves (radiowaves and/or light) and/or by mechanical waves. The system may be equipped with an electromagnetic transmitter configured to transmit signals in order to request additional information from surrounding devices. For example, a Bluetooth communication module of a car may be used to identify a driving activity. Further, radiation of the Bluetooth module of a smartphone or a tablet may be used to identify the activity of using a handheld device. Since Bluetooth modules typically broadcast the numerical (MAC address) and text identifiers of the device, a database can be used to associate the device with a specific activity. For example, the car may broadcast the text identifier of the car model and maker, while the smartphone by default may broadcast a maker and model of the phone, which may be associated with activity. The additional information, such as identifier of the device or device location or device type may be requested by the system by transmitting request signals by means of a transmitter. The properties of the signal, such as signal strength, signal delay, signal reflections may be used to improve classification of vision activity.

The context sensor may be equipped with the positioning/location sensor, configured to provide information about the position and movement (speed, acceleration and trajectory) of the user. The positioning sensor may be one of global positioning systems, like GPS, GLONASS, GNSS, or local positioning systems or indoor positioning systems. The indoor positioning system may be implemented by scanning wireless devices around the system, for example WLAN or Bluetooth emitting devices. Position and movement of the user may be used by the classifier to classify the corresponding activity. For example, the user walks. Combining this information with the motion data showing a characteristic walking pattern, the classifier may conclude that the user is walking.

The visual field sensor as well as the head orientation/position sensor can be used as a context sensor as well.

The context parameter measured by the context sensor may be used for automatic identification of vision task in combination with at least one other context parameter, different from the first one and measured with the same or different context sensor. At least two context parameters from the same or different context sensors can be used together for the identification of activity/task or the object related thereto.

The vision task may be identified automatically based on at least one of the visual field parameter measured by the visual field sensor, characteristic points cloud, head orientation, movement pattern, illumination conditions and context sensor readings. Identification of activity/task, or classification may be performed using statistical analysis of data, for example by methods of machine learning with classifier trained on the data measured during known/labelled or tagged activities. Such methods may include logistic regression, naïve Bayes classifier, Fisher's linear discriminant, support vector machines, k-nearest neighbour, decision trees, random forests, neural networks, or any other known method or combination of multiple methods.

The data of the visual field sensor can be used in original dimensionality and resolution or can be reduced to improve the stability of an underlying classification algorithm. For example, the visual field sensor utilizing the directional sensor may construct the map of objects of the visual field. For example, handheld reading material, such as book, tablet or smartphone may be recognized as a points cloud forming a plane with known size in two-dimensional or three-dimensional map. When the object of matching shape and size is detected, accompanied by characteristic head tilt, the reading of handheld media may be detected.

Additional sensors may improve the accuracy and specificity of classification. For example, a sensor capable of detecting a polarization state of reflected light may be used to differentiate liquid crystal based display of the handheld electronic devices from the paper-based media such as books. Additionally or alternatively, the directional sensor may be used to detect light emitted by electronic devices to achieve the same. Additionally or alternatively, a motion sensor may be configured to detect head movements associated with reading in order to differentiate reading of handheld material from watching media content, such as movies on handheld electronic devices. Additionally or alternatively, a light sensor capable of detecting temporal variations of light caused by dynamic media content, such as a movie, may be used to enable differentiation of reading and watching activity.

The system may include a database of original measurements or statistically processed measurements performed during known activities/tasks. Thus, unknown activity/task can be identified by comparing measurements with the measurements from the database. In a similar way, identification of the object in the visual field may be performed automatically with methods of statistical analysis/modelling. The database of signature measurements of known objects may be composed and further object identifications may be performed by comparing measurements of unknown objects with the measurements of known objects stored in a database.

The visual field of a user may be defined as the field of view of the user. The user may be a patient or a wearer of an optical aid, such as lenses, spectacles, or someone who is to receive a modification or replacement of an optical element of an eye. The optical aid may also be a device which primary aim is not to compensate insufficiencies of vision but to enhance vision with elements beyond the function of the normal human vision. For example, such enhancement can be provided with the virtual/augmented/mixed reality headset or smart glasses, which modify the normal visual field in order to provide extra functionality, such a display of elements of graphical user interface, highlighting of objects in visual field, adding artificial objects to the visual field and so on. It is to be understood that such device may still provide compensation of vision insufficiencies such as myopia, hyperopia, presbyopia and others.

The gaze direction is defined by the direction to the point which is viewed by the eyes from a common coordinate axis. The gaze direction may also be understood as gaze angle. In two-dimensional view, when bilateral symmetry of the visual task/activity can be assumed, the common coordinate axis may be the horizontal plane and the gaze angle is defined by a single pitch angle. The gaze angle may be constructed by an inclination angle of the head (head pitch angle) and an inclination angle of the eyes with respect to a head angle.

The gaze direction/angle may be derived from a position of the object related to the visual task in a common coordinate system. The common coordinate system may be a spherical coordinate system. The spherical coordinate system may have its origin at a root of a nose or another point of the user.

The projection surface may be defined as a surface related to the function of the optical aid. For example, the projection surface may define the surface where the optical aid to be used later is to be positioned with respect to the user's eyes. The projection surface may be defined within the volume of the optical aid as well as outside it. The projection surface may be a flat plane, a spherical surface, a toric surface, or any other surface inbetween the user's retina and the visual field. The surface may be virtual/virtually, for example not associated with a surface of an entity.

The projection surface can be positioned outside of the eyes, for example, when the projection surface is a spectacles plane, where the lenses of spectacles are placed or the surface can be a screen plane or optics plane of the virtual/augmented/mixed reality headset or glasses. It may then be fixed in a coordinate system of a head. The projection surface can also be positioned on the surface of the eye or inside of the eye, which is the case for a contact lens or ophthalmic implant. The projection surface on the surface of the eye may be linked to the head coordinate system, while the eye(s) of the user may move in relation to the projection surface. This is the case of a segmented bifocal or multifocal contact lens, which remains in place even when the eye(s) of the user move.

In an example, the contact lens as well as ophthalmic implant may move together with the eye and the eye projection surface is fixed at the coordinate system of the eye(s). Since an individual coordinate system may be assumed for each eye, the projection surface may be individual for each eye.

Further, the projection process can be equally applied to the head-centred projection surface, as well as eye-centred projection surface.

In one example, projection may take into account individual characteristics of the user. These may include inter-pupillary distances, shape of the face/nose which may affect position and angle of the spectacles plane on the head, geometry and parameters of the eye structures, such as corneal curvature, range of the pupil size, position of the natural lens, length or other dimensions of the eye, etc.

Additionally or alternatively, projection may incorporate further optical parameters of the user's eye(s) which may be influenced by the visual field. These may include eye rotation in the orbit, adjustment of the pupil size to the illumination level of the visual field, accommodation of the natural lens to bring visual field in focus, closing and/or opening of the eye lid.

Projection may be performed by ray tracing, when the path of light from objects of the visual field is traced based on physical rules of the light propagation. Preferably, the light may be traced from the object until reaching the retina of the user.

Propagation of light from the object through the projection surface on the way to the retina may define the locus of object on the projection surface. The projection may be formed by the rays reaching the retina and forming the image on the retina.

The projection may be performed with simplified methods of mathematical and geometrical transformations.

Mapping may be performed by geometric projection: relating coordinates of the visual scene to the coordinates on the projection surface. For example, position of the centre of a smartphone display in the visual field may be translated into the position of the point in a spectacles plane. Additionally or alternatively, limiting optics may be taken into account for mapping. For example, the pupil size may affect the active area of contact lenses, corneal implants and/or intraocular lenses. When the pupil is constricted, light can reach retina through central zone of the visual aid only, while a dilated pupil may increase an aperture of the visual aid and involves peripheral optical zones of the lens. This relation may be considered for customization of multifocal lenses, which has the optical power changing with distance from the centre. For example, the user may be mainly utilizing distance vision in the outdoor, well lid conditions, while utilizing near vision indoors with relatively limited illumination. The pupil-constricted mapping may produce a mix of near and far distances (and corresponding optical powers) in the central zone of the visual aid, since in both near and far activities light passes through a central zone.

The near distance activity associated with limited illumination may also be mapped on the concentric peripheral zones.

In this case customization can be achieved by optics facilitating distance vision in the centre, matching the conditions of constricted pupil in the outdoor setting, and placing optics facilitating near vision in the periphery in such a way that near zone opens when pupil dilates in the low light conditions.

Customisation may take into account the performance of the optical system of the eye and defocus tolerance based on the eye geometry. With the constricted pupil the depth of focus may be increased, which may enhance the range of distances formed in focus at the retina. Thus the requirement of optical power accuracy in the central zone of the visual aid may be lower than in the peripheral zones.

Mapping may combine measurements performed during multiple vision tasks/activities. It can be envisaged that user is performing measurements continuously, effectively combining typical daily vision tasks.

The system may be a head mounted wearable adapted to be worn by the user. In particular, the wearable may be a single module comprising all the elements or sensor devices/units of the system. Thus, the visual field sensor and the head orientation and/or position sensor may be in the same housing.

Thus, the system may be compact and reduced in power consumption as well.

Coordinate systems of the respective head orientation and/or position sensor and the respective visual field sensor may be aligned. In consequence, a coordinate transformation may be avoided. Computational steps can be reduced consequently.

The coordinate systems of the respective head orientation and/or position sensor and the respective visual field sensor may be the same or may have a same reference point. Thus, only rotational information may be needed for transforming the one into the other.

The visual field sensor and the head orientation and/or position sensor may be separated from each other.

In consequence, the system may be provided in modular form. For example, the visual field sensor may be operated or deposited at a desk, a shelf, a board or another deposit. The head orientation and/or position sensor may be head mounted instead. Thus, in order to not have a bulky device at the head, the system can be provided modularly in this way.

In a modular implementation of the system, the visual field sensor may be mounted on a body part of the user, different from a head, for example a torso, while the head orientation and/or position sensor may be head mounted.

Measurements of the visual field sensor and head orientation and/or position sensor may be synchronised in order to correctly link head orientation and/or position to the objects of the visual field. Synchronisation may be performed in a real time of the measurements, by triggering or reading out the measurements of both sensors simultaneously or within a predefined time period which may be (negligibly) small. Synchronisation may be performed by recording measurements of both sensors independently, but with information allowing to link the recorded measurements to the time. For example, in a modular implementation, the visual field sensor and head orientation and/or position sensor may have an onboard clock, which can be related to the common time point, and the measured data is recorded together with corresponding timestamp. On the processing stage the measurements of both sensors may be linked to the common time system.

The same applies to the context sensor: it may be synchronised with other sensors in real-time or may have an independent clock, which can be related to the common time point.

The head orientation and/or position sensor may be coupled to the visual field sensor. The head orientation and/or position sensor may be adapted to provide positioning information of the visual field sensor to transform positioning information from a coordinate system of the head orientation and/or position sensor into a coordinate system of the head orientation and/or position sensor. The transformation may be performed by the processing unit. Thus, the processing unit and the head orientation and/or position sensor may be in communication with each other. This communication may be direct via a cable or indirect via communication means such as an antenna system driven short range communication system, such as Bluetooth or wireless local area network (WLAN). The head orientation and/or position sensor may thus have an interface for connecting to a standard WLAN device. This interface may be shared by the head orientation and/or position sensor and/or the processing unit. The position of the processing unit may be within a single device together with at least the head orientation and/or position sensor. Inside the single device, the visual field sensor may be located as well. However, the processing unit may be provided as a separate unit. For example, the processing unit may be provided via a network on a (foreign) server or over the cloud. Thus, the processing by the processing unit may be performed on a device which is only in communication with at least one of the other elements of the system, such as an interface of the system for communication or for connecting communication means to the system.

The projection surface may be associated with and/or linked to an optical aid.

For example, the projection surface may be a plane at which the optical aid is to be positioned or used later. Thus, the projection surface may be the plane of the optical aid. The optical aid may for example be spectacles, a lens, or a surface of the eyes.

In consequence, optical powers and pupil diameters may be considered at specific distances from the user's eyes.

According to a second aspect, a use of the system according to the first aspect is provided. The optical parameter distribution on the projection surface is used for customization of an optical aid. The optical parameter may be at least one of optical powers, pupil diameters, depths of focus, spectral content of light, angular distribution of light, and polarization state of light. The optical parameter distribution may comprise a distribution of optical parameters on the projection surface.

The optical parameter distribution on the projection surface to be used later for the optical aid may comprise a combination of both the pupil diameter and the optical powers. Thus, illumination requirements and power requirements of the individual can be taken into account simultaneously.

Pupil diameter/size may be estimated from illumination conditions, such as intensity and spectral content of light using empirical formulas and/or models. Such formulas may include other parameters of the environment as well as personalized coefficients. Models may be general or personal. Pupils diameter/size may be further used to calculate depth of focus of vision. Depth of focus may be used to optimise customization of optical aid.

When a number of activities have been recorded requiring different optical powers with different depth of focus, a combined solution can be found by combining optical powers and depth of focus. For example, an activity A is performed at the distance 1 m in the bright illumination. This leads to an optical power requirement of 1D and depth of focus corresponding to constricted pupil, which may be 0.5D, so the range of optical powers is 0.75-1.25D. For example, an activity B is performed at distance 1.25 m at low light and thus the required optical power is 0.8D and the depth of focus corresponds to constricted eye, which is around 0.1D, so the range is 0.75-0.85D. Since the customization of the optical aid should be able to provide best vision for the most of the visual activities, the acceptable power range may be 0.75-0.85D, which would satisfy requirements of both activities A and B.

According to a third aspect, a method for determining an optical parameter distribution at a projection surface is provided. The method comprises measuring, by a visual field sensor, a visual field of a user related to a specific vision task. This may include identifying, by the visual field sensor, an object related to the specific vision task in the visual field of the user. The method further comprises determining, by the visual field sensor, gaze directions of the user during the specific vision task. The method further comprises measuring, by a head orientation and/or position sensor, head orientation and/or position of the user in relation to the visual field during the specific vision task, e.g. head angles of the user associated with the gaze angles during the specific vision task. The method may comprise enabling computation of the user's eye orientation in relation to the head of the user based on the gaze directions of the user and the head orientation and/or position of the user to determine an optical parameter distribution at a projection surface between the visual field and a retina of the user. For example, the method further comprises enabling computation of corresponding differences between the head angles and the gaze angles to determine an optical parameter distribution at a projection surface between the visual field and a retina of the user.

According to a fourth aspect, a computer program product is provided comprising program code portions for carrying out a method according to the second aspect when the computer program product is executed on one or more processing units.

According to a fifth aspect, a computer program product according to the third aspect stored on one or more computer readable storage media is provided.

According to a sixth aspect, an optical aid is provided. The optical aid may be an adjustable optical aid. The optical aid can be adjusted/is adjustable based on a method according to the third aspect or based on using a system according to the first aspect.

Even if some of the aspects described above have been described in reference to the system, these aspects may also apply to the method. Likewise, the aspects described above in relation to the method may be applicable in a corresponding manner to the system.

It is clear to a person skilled in the art that the statements set forth herein under use of hardware circuits, software means or a combination thereof may be implemented. The software means can be related to programmed microprocessors or a general computer, an ASIC (Application Specific Integrated Circuit) and/or DSPs (Digital Signal Processors).

For example, the sensor unit herein, such as the head orientation and/or position sensor, the visual field sensor, the processing unit and the context sensor may be implemented partially as a computer, a logical circuit, an FPGA (Field Programmable Gate Array), a processor (for example, a microprocessor, microcontroller (μC) or an array processor)/a core/a CPU (Central Processing Unit), an FPU (Floating Point Unit), NPU (Numeric Processing Unit), an ALU (Arithmetic Logical Unit), a Coprocessor (further microprocessor for supporting a main processor (CPU)), a GPGPU (General Purpose Computation on Graphics Processing Unit), a multi-core processor (for parallel computing, such as simultaneously performing arithmetic operations on multiple main processor(s) and/or graphical processor(s)) or a DSP.

It is further clear to the person skilled in the art that even if the herein-described details will be described in terms of a method, these details may also be implemented or realized in a suitable device, a system, a computer processor or a memory connected to a processor, wherein the memory can be provided with one or more programs that perform the method, when executed by the processor. Therefore, methods like swapping and paging can be deployed.

It is also to be understood that the terms used herein are for purpose of describing individual embodiments and are not intended to be limiting. Unless otherwise defined, all technical and scientific terms used herein have the meaning which corresponds to the general understanding of the skilled person in the relevant technical field of the present disclosure; they are to be understood too neither too far nor too narrow. If technical terms are used incorrectly in the present disclosure, and thus do not reflect the technical concept of the present disclosure, these should be replaced by technical terms which convey a correct understanding to the skilled person in the relevant technical field of the present disclosure. The general terms used herein are to be construed based on the definition in the lexicon or the context. A too narrow interpretation should be avoided.

It is to be understood that terms such as e.g. "comprising" "including" or "having" etc. mean the presence of the described features, numbers, operations, acts, components, parts, or combinations thereof, and do not exclude the presence or possible addition of one or more further features, numbers, operations, acts, components, parts or their combinations.

The term "and/or" includes both combinations of the plurality of related features, as well as any feature of that plurality of the described plurality of features.

In the present case, if a component is "connected to" or "in communication with" another component, this may mean that it is directly connected to or directly accesses the other component; however, it should be noted that another component may be therebetween. If, on the other hand, a component is "directly connected" to another component or "directly accesses" the other component, it is to be understood that no further components are present therebetween.

Other objects, features, advantages and applications will become apparent from the following description of non-limiting embodiments regarding the accompanying drawings. The same or similar components are always provided with the same or similar reference symbols. In the description of the present disclosure, detailed explanations of known connected functions or constructions are omitted, insofar as they are unnecessarily distracting from the present disclosure. In the drawings, all described and/or illustrated features, alone or in any combination form the subject matter disclosed therein, irrespective of their grouping in the claims or their relations/references. The dimensions and proportions of components or parts shown in the figures are not necessarily to scale; these dimensions and proportions may differ from illustrations in the figures and implemented embodiments. In particular, in the figures, the thicknesses of lines, layers and/or regions may be exaggerated for clarity.

Figure 2:
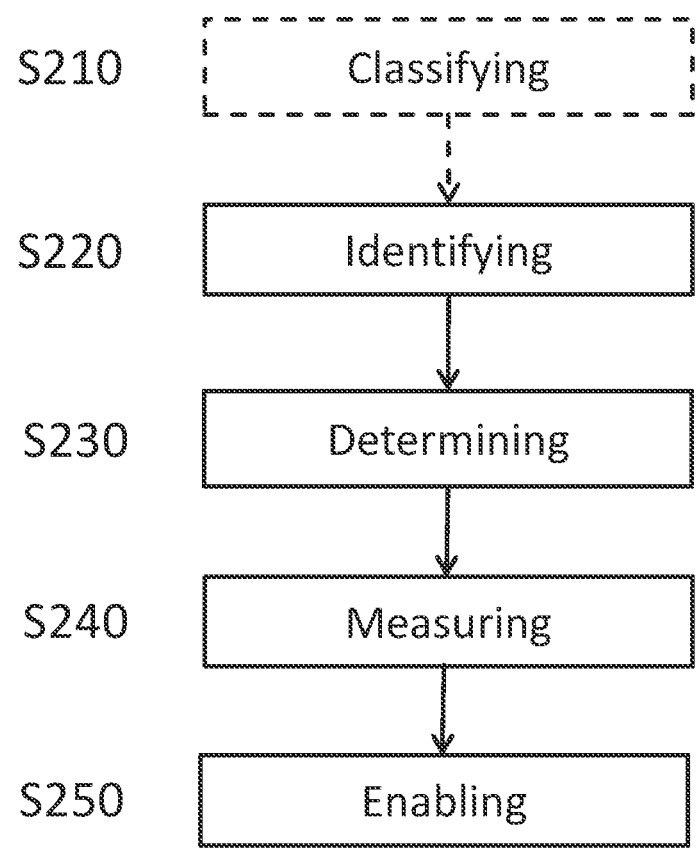
Figure 3:
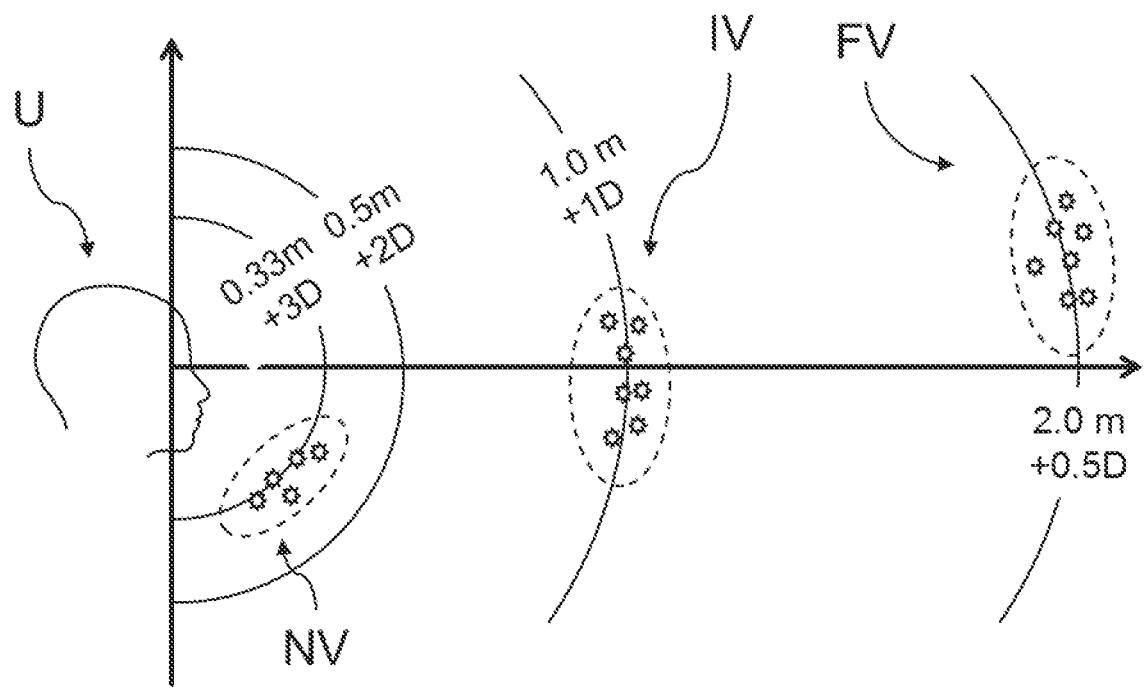
Figure 4:
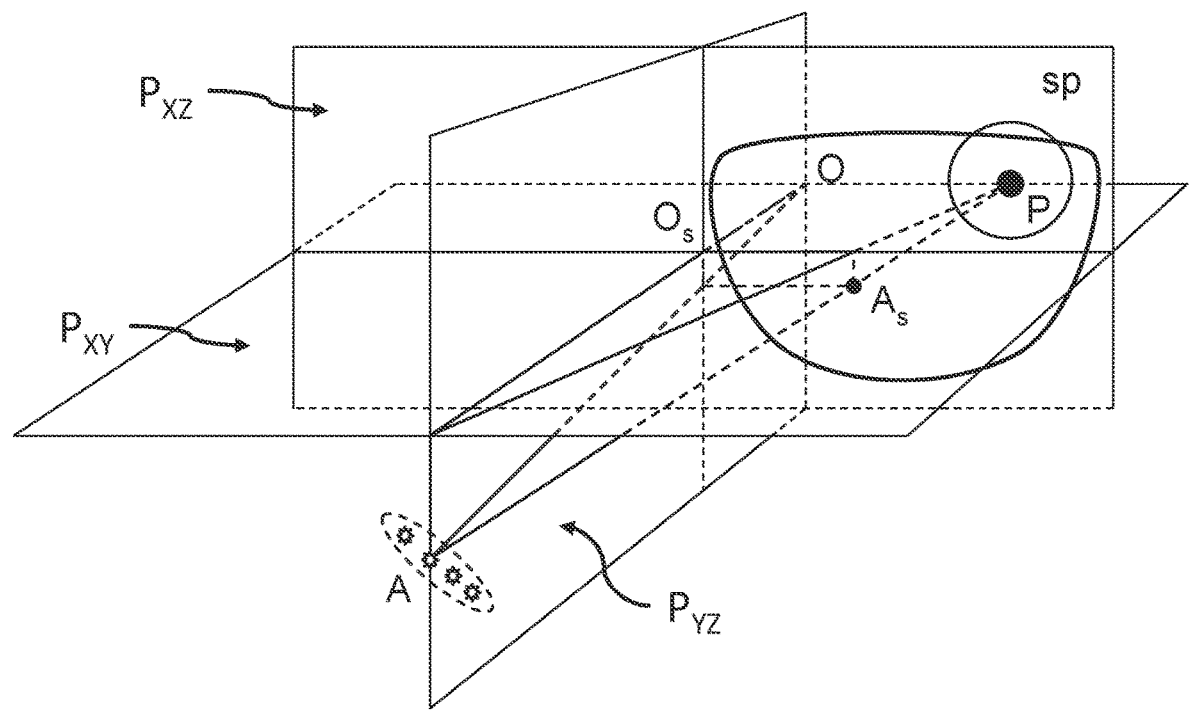
Figure 5:
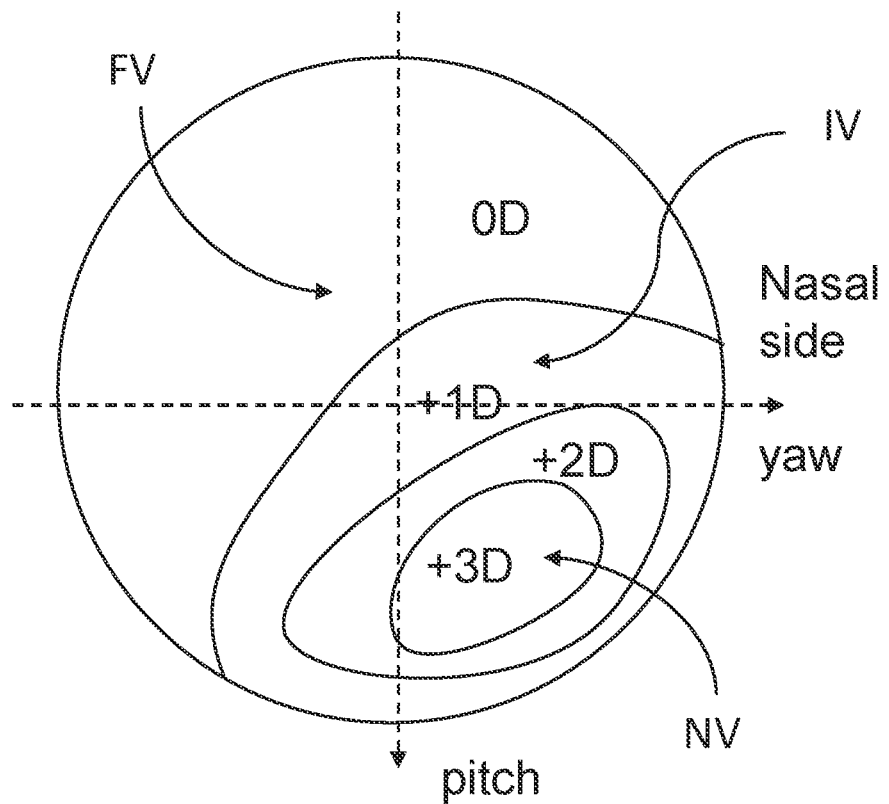
Figure 6:
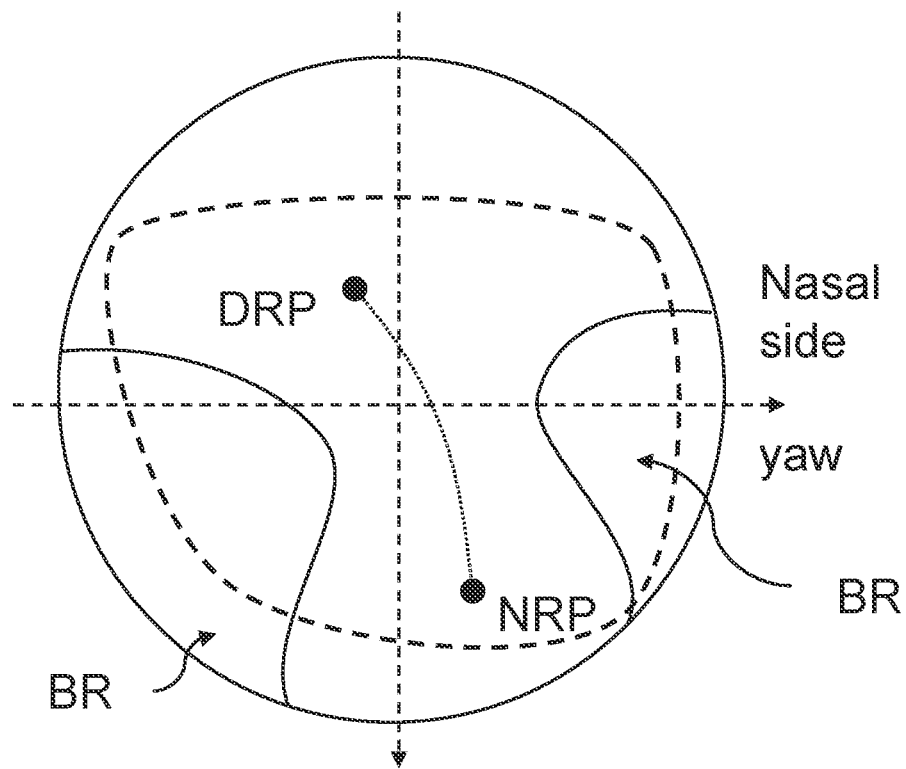
Figure 7:
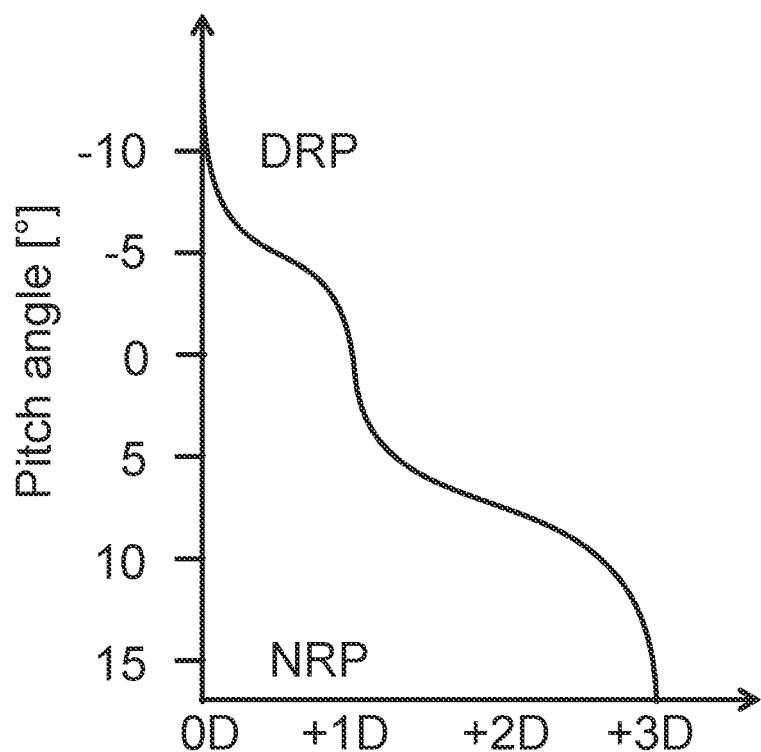

FIG. 1 schematically illustrates a scenario where a system for determining an optical parameter distribution at a projection surface is used;

FIG. 2 schematically illustrates a method for determining an optical parameter distribution at a projection surface;

FIG. 3 schematically illustrates point clouds in a coordinate system of a user's head;

FIG. 4 schematically illustrates a coordinate system of the head and mapping of the object in sagittal plane into the spectacles plane;

FIG. 5 schematically illustrates a requirement for power distribution in form of a power map at an optical aid's plane corresponding to the right eye;

FIG. 6 schematically illustrates a possible implementation of a power distribution/profile of an optical aid as an example of progressive addition spectacles lens;

FIG. 7 schematically illustrates an example of a power profile; and

Figure 8:
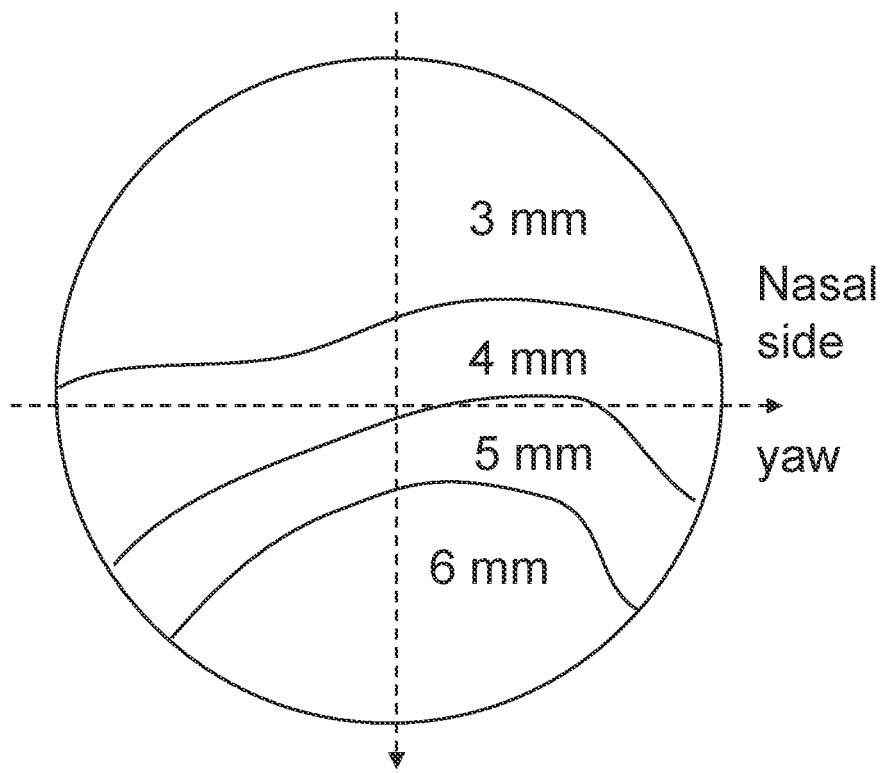

FIG. 8 schematically illustrates a projection of pupil diameters at an optical aid's plane.

The system and the method will now be described with respect to the embodiments. In particular, without being restricted thereto, specific details are set forth to provide a thorough understanding of the present disclosure. However, it is clear to the skilled person that the present disclosure may be used in other embodiments, which may differ from the details set out below.

FIG. 1 schematically illustrates a scenario 100 where a system for determining an optical parameter distribution at a projection surface is used. At least part of the system is arranged in the device 110. The device 110 may include a head orientation and/or position sensor. In particular, the head orientation and/or position sensor in FIG. 1 can be one dimensional due to the sagittal view of the illustrated head 150. The head orientation and/or position sensor measures the head's 150 orientation in the sagittal plane as shown in FIG. 1. However, this may be extended to all planes with the respective sensor equipment inside the head orientation and/or position sensor of the device 110. So, the head orientation and/or position sensor may be calibrated to measure a head angle $\beta=0$ when the head does not tilt with respect to the horizontal. This is specifically shown in FIG. 1.

When viewing of objects requires a gaze angle ($\alpha$) below the horizontal plane of the eyes 170, the head inclination ($\beta$) (also referred herein as head angle) is only partially contributing to the gaze angle ($\alpha$). The remainder ($\gamma$) comes from reorienting the eyes 170 (only eyes' 170 inclination) with respect to the head's inclination $\beta$. This is performed by the body itself in order to reduce the load on the neck 160. The distribution of angle contributions between head 150 and eyes 170 is individual and also depends on the individual position of the object 130 which may be specific to the activity and user. The object 130 in FIG. 1 is a handheld media and is looked upon by the user, illustrated by the head 150. The device 110 may be worn by the user, in particular at the user's head or the user's temple. Further to this, the device 110 may be a head mounted wearable. The device 110 may be integrated into a spectacles frame or mountable thereon.

Further to the head orientation and/or position sensor, the device (e.g. wearable device) may incorporate at least one distance sensor, which is able to measure distances to the object 130 in the visual field 120. The visual field 120 is indicated by the arrows and stars in FIG. 1. The distance sensor may be part of the visual field sensor described herein or the visual field sensor may be in the form of a distance sensor described with respect to FIG. 1. Since the head and the body of healthy individuals are rarely in complete rest during an awake state, a distribution of head inclination angles is expected during a period of observation. With the distance sensor performing multiple measurements separated in time it is possible to obtain distances to the object 130 within the visual field 120 in various directions from an observation point (head's view). This may be the reference of the head coordinate system.

Sampling of the environment (the visual field 120) may be performed by at least one directional distance sensor. The distance sensor may be a wearable distance sensor coaligned with the head of the user and/or integrated in the device 110. The distance sensor may have scanning means or angle/space resolved sensor, however, the distance sensor may also exclusively rely on natural head movements of the user in order to sample the environment in different directions or may be a combination of different means of sampling in different directions. By relating distance measurements to the orientation or position of the device 110 it is possible to construct a two or three dimensional point cloud representing an environment in relation to the head orientation and the position of the user. Initial orientation or position of the device 110 may be obtained from inertial (e.g. accelerometer, gyroscope, magnetometer) sensors or location sensors incorporated in the device 110.

In order to automatically identify activities, additional context sensors can be used. For example, a motion sensor can sample user's motion intensity and statistical characteristics. For example, specific signature movements can be recognized, for example a movement of the head 150 while reading. The context sensor(s) may also be included in the device 110.

Activities may be automatically identified with help of external sensors or with direct user input performed via user interface as a part of the wearable and/or system and/or additional device, such a mobile phone or internet interface. The input identifying activity can be performed in real time or later. For example, the user might be able to review history of measurements via interactive interface implemented as a web page or mobile application and link time series to specific activities.

An example of such input can be: from 10:00 till 10:30 activity was Reading, from 10:30 till 10:45 activity was Walking, from 10:45 till 11:45 activity was Driving and so on.

Identification of activities can also be performed as a combination of automatic and manual input. For example, the system may only request user input when the confidence or other metric of performance of automatic identification is below certain threshold. In the example above, the system may be able to automatically identify Reading and Driving (confidently), but may have some concerns regarding Walking and thus may request a user input. The system may be further configured to use user input on the single episode of activity to update automatic identification of other episodes. In the example above, the user may manually specify the single episode of Walking between 10:30 and 10:45 and the system may automatically update the activity classifier and re-evaluate all remaining episodes.

The head orientation and/or position sensor may comprise an accelerometer. In the simplest case the single axis accelerometer may be used which is capable of measuring projection of acceleration vector on a single axis. The single axis of the accelerometer can be aligned horizontally with the device 110 in such a way that when the user is looking straight forwards ($\beta=0$), the accelerometer measures zero acceleration, since the projection of vector g (gravitational acceleration) on axis x is zero ($g_x = g \sin \beta = 0$, g is an absolute value of vector g). When the head 150 of the user is tilted forwards ($\beta>0$) projection $g_x$ becomes positive. The head inclination angle $\beta$ can be calculated from the measured projection yielding $\beta = \arcsin g_x/g$. The accelerometer sensor can measure acceleration along the axis z acting on the device 110 (head orientation and/or position sensor coordinate system). In the absence of significant acceleration of the device 110 caused by motion (which is expected during important visual activities) the accelerometer measures gravitational force and thus acceleration g.

The vertical angle (pitch) of the head $\beta$ can be derived from the measurements of gravitational force by the accelerometer (at least one axis) mounted on the head 150 (for example on spectacles or at the temple of the user). In a more advanced configuration the head orientation and/or position sensor may include a 3-axis gyroscope, a 3-axis accelerometer and a 3-axis magnetometer (for example a compass). Then it is possible to estimate absolute angles of the head orientation and/or position sensor and, correspondingly, absolute orientation of the head 150, when the head orientation and/or position sensor is fixed to the head 150 of the user.

Additionally or alternatively, the head position sensor is capable of monitoring the position of the head in relation to the visual filed or vison field sensor.

A position of the object 130 of interest (object related to a specific visual activity) can be found by observing the visual field 120 with the visual field sensor in relation to the axes of the head 150. For example, this can be performed by a head mounted camera, also called point-of-view (POV) camera, a POV distance sensor or a space-resolved distance sensor (3D camera). By detecting object(s) of interest in the visual field it is possible to indirectly derive angles ($\alpha$, $\beta$, $\gamma$) and positions (x, y, z) of the alignment of the object(s) in the visual field.

In combination with distances measured by the distance sensor, the positions of points can be obtained in the sagittal plane of the body and form a point cloud (points in FIG. 1 of visual field 120) of an object 130 in the visual field 120. Further, the recognition of the object 130 can be performed based on the expected visual field 120 if the type of vision task is already given (for example, if the user has provided information via a user interface) or the type of activity can be recognized automatically by comparing statistics of measured distances (obtained by the visual field sensor/distance sensor) with a dataset of statistical signatures of visual activities.

For example, the identified or recognized activity is reading from handheld device 130, as in the example shown in FIG. 1. In this case the primary object of visual activity is reading the handheld device 130, which has a flat surface and thus would appear as a line in the sagittal plane projection in the comfortable arm reach distance. Points corresponding to such a definition are marked with a dashed line (see FIG. 1). The angles corresponding to the points on the object 130 of primary visual activity are further defining the set of gaze angles $\alpha$ used by the user to perform the corresponding vision task. Since the angle $\beta$ of head inclination is known from head orientation and/or position sensor mounted on the head 150 it is possible to estimate eyes' 170 shifts/angles $\gamma = \alpha - \beta$.

The density of the point cloud and the scanning range can be increased by adding further distance sensors with orientation and/or positions different from the visual field sensor or by using sensors which are able to obtain samples in the plurality of directions. For example, these sensors may have a single emitter and plurality of sensitive zones/detectors, with different sensitivity to distance in different directions. This can be achieved by sensor design or with additional elements, for example with optical elements if the sensor is optically based.

For example, this is implemented by a laser ranging sensor having a 16×16 array of single-photon avalanche diodes (SPAD), which can be configured to select a required region of interest. This implements a single emitter-multiple detectors strategy.

Another example may incorporate a camera or an array of detectors arranged in such a way that they detect light coming from different geometrical positions or/and directions.

In a further example, the distance sensor may have at least one detector and a plurality of emitters configured to emit light to different directions and/or positions. In this case the detector is configured to detect light emitted by at least one of the emitters and reflected from the visual field 120. The configuration/arrangement of active emitters may change from one time point to another, which allows collecting spatially resolved information.

In another example, at least one emitter can be configured to change the direction of emitted light in order to probe the visual field 120 at different directions/positions.

This can be achieved, for example, by a scanning element, which can be a scanning mirror, scanning prism or other moving optical element configured to modify the optical path of emitted light in order to emit probing light in different directions. The detector may then be configured to detect light reflected from objects probed by emitter radiation. The signal of detector can be linked to the information about the probed direction/position in order to reconstruct the visual field 120. These directions may be known a priory from a design of the scanner, obtained in the calibration step or obtained during a scan with additional feedback signal.

Alternatively, the visual field can be monitored by the visual field sensor when physically/mechanically decoupled from the head orientation and/or position sensor and head. For example, the visual field sensor can be mounted on the body of the user (e.g. on a torso and/or chest) or it can be mounted outside of body (e.g. on a desk or on a dashboard of a car). The head orientation and/or position sensor and the visual field sensor may have means of relating coordinate systems of each other, in particular orientations and/or positions to each other. For example, this can be achieved with additional orientation and/or position sensor(s) mechanically coupled to the visual field sensor.

Another approach may be limiting relative movement of visual field sensor and head. For example, by mounting visual field sensor at a specific part of the body, different from the head, for example at the chest, in such a way that relative movements of visual field sensor and a head can only be caused by the head inclination, e.g. pitch, yaw, roll, which can be monitored with the head orientation and/or position sensor.

More details and aspects are mentioned in connection with the embodiments described above or below. The embodiment shown in FIG. 1 may comprise one or more optional additional features corresponding to one or more aspects mentioned in connection with the proposed concept or one or more embodiments described below (e.g. FIGS. 2-8).

FIG. 2 schematically illustrates a method for determining an optical parameter distribution at a projection surface. The method may as a first step include classifying S210 the visual task. Thereafter, the method comprises measuring S220, by a visual field sensor, visual field of a user related to a specific vision task. This may include identifying an object related to the specific vision task in the visual field of the user. The method further comprises determining S230 gaze directions of the user during the specific vision task. The method further comprises measuring S240, by a head orientation and/or position sensor, head orientation and/or position of the user in relation to the visual field during the specific vision task. The method further comprises enabling S250 computation of the user's eye orientation in relation to a head of a user based on the gaze directions of the user and the head orientation and/or position of the user to determine an optical parameter distribution at a projection surface between the visual field and a retina of the user.

In particular, the method may be performed in two different ways. The first way is based on mechanically coupled visual field sensor, like the distance sensor as described with respect to FIG. 1, and head orientation and/or position sensor. The method as shown in FIG. 2 may therefore comprise at least one of the following (additional) steps according to the first way of performing the method:

obtaining S205 a point cloud of one or more objects in a visual field of a user;
    classifying S210 the type of a vision task;
    identifying S220 at least one relevant object related to a specific vision task in the visual field by the visual field sensor; and
    calculating S230 at least one of the components of a gaze angle (pitch, yaw and/or roll in a common coordinate system) corresponding to at least one relevant object of vision task;
    measuring S242 (S240) a head orientation by a head orientation and/or position sensor during the visual activities;
    calculating S244 (S240) at least one component of the head angle (pitch, yaw and/or roll in the common coordinate system); and
    calculating S250 at least one angle between a head and objects (eyes' angles) as the difference between the gaze direction and head orientation and/or position Recognition of the objects is easier to perform in the geocentric coordinate system, since objects of the visual activity are often arranged in the real space in relation to the gravitational field, for example, papers on the desk, computer displays, screens of television sets, dashboards of the car.

The second way is based on a mechanically decoupled visual field sensor and head orientation and/or position sensor. The method as shown in FIG. 2 may therefore comprise at least one of the following (additional) steps according to the second way of performing the method:

identifying S220 one or more objects in a visual field of the user by a visual field sensor and calculating S230 a gaze angle (in the common coordinate system)
    measuring S240 a head orientation by a head orientation and/or position sensor during the visual activities and calculating the head angle (in the common coordinate system)
    calculating S250 at least one angle between the head and objects (eyes' angles) as the difference between the gaze angle and head angle.

More details and aspects are mentioned in connection with the embodiments described above or below. The embodiment shown in FIG. 2 may comprise one or more optional additional features corresponding to one or more aspects mentioned in connection with the proposed concept or one or more embodiments described above (e.g. FIG. 1) or below (e.g. FIGS. 3-8).

FIG. 3 schematically illustrates point clouds in a coordinate system of a user's head. In particular, a sagittal plane is shown for comprehensiveness. Points cloud can be obtained by combining measurements of at least single-directional distance sensor with the measurements of orientation and position of the sensor. Measurements from multiple distance sensors (for example, probing different directions) can be combined in one map, or can form multiple maps. When at least a pitch angle of the head inclination is measured, points clouds are defined in the two dimensional sagittal plane. With the use of additional orientation sensors, such as gyroscope and/or magnetometer, it is possible to add yaw and roll angles of the head and define points clouds in three-dimensional space. For example, by classifying the visual task or activity, gaze angles can be extracted accordingly. In the sagittal plane, the points corresponding to respective gaze angles are all lying in particularly the same distance from the head U depending on the visual task. FIG. 3 shows points cloud corresponding to near vision (NV) task, such as reading a book or looking on the smartphone, in this example at the distance around 0.33 m, corresponding to 3D refraction, another cloud is in the intermediate vision (IV) zone around 1 m (1D refraction), which could be viewing desktop computer display and cloud in far vision (FV) zone around 2 meters (0.5D), which could be watching TV.

Point clouds may be forming patterns characteristic to the activity. Shape and/or position of point clouds may be used to classify visual activities automatically. The classification may be in combination with a user input of what type of visual task the user performs and/or in combination with pattern recognition from a video taken during the visual task and/or in combination with measurements of the other sensors. For example, the visual field sensor may be a camera, and the processing involves finding objects from 2D images, for example, identifying books or handheld devices (smartphones or tablets), computer screen. This involves understanding of user's activities by camera images.

More details and aspects are mentioned in connection with the embodiments described above or below. The embodiment shown in FIG. 3 may comprise one or more optional additional features corresponding to one or more aspects mentioned in connection with the proposed concept or one or more embodiments described above (e.g. FIGS. 1-2) or below (e.g. FIGS. 4-8).

FIG. 4 schematically illustrates a coordinate system of the head and mapping of the object in sagittal plane into the spectacles plane. Placing of objects in sagittal plane can be assumed when the activity is bilaterally symmetrical. Examples of such activities include reading the handheld media, such as a book, working on a desktop computer, working on workbench, etc. In this case the distances to the objects may be monitored together with head's pitch angle without regard to yaw and roll. Example can be activities presented in FIG. 3.

The respective coordinates of points of the point cloud (here point A) associated with the specific visual task are recalculated to the coordinate system of the head. In particular, optical parameters, such as the optical power, are mapped to a projection surface, which may be a spectacles' plan.

FIG. 4 specifically illustrates the following numerals:
$P_{xz}$—spectacles plane;
$P_{yz}$—sagittal plane;
$P_{xy}$—perpendicular plane to $P_{xz}$ and $P_{yz}$;
P—eye pupil position;
A—point of the object;
$A_s$—image of object point on the spectacle plane;
O—root of the nose;
$O_s$—projection of O on spectacles plane;
$OO_s$—vertex distance; and
OP distance—monocular pupillary distance adjusted to vergence.

Further, a panoscopic tilt (lens pitch) and wrap angle (lens yaw) can be taken into account for customizing the specific optical aid.

In a more general case of activity, the bilateral symmetry cannot be assumed (e.g. during car driving). In this case monitoring of head orientation can be performed in all three angular dimensions: pitch, yaw and roll. The points cloud is not limited to sagittal plane and defined in the 3D space. The illustrated geometrical model can be further extended to allow rendering to the projection surface.

More details and aspects are mentioned in connection with the embodiments described above or below. The embodiment shown in FIG. 4 may comprise one or more optional additional features corresponding to one or more aspects mentioned in connection with the proposed concept or one or more embodiments described above (e.g. FIGS. 1-3) or below (e.g. FIGS. 5-8).

FIG. 5 schematically illustrates a requirement for power distribution in form of a power map at an optical aid's plane corresponding to the right eye. For example, such distribution can be obtained from points clouds in FIG. 3 with geometrical transformation shown in FIG. 4. In this case the near vision (NV) zone yields a requirement to optical aid of having a zone with optical power of 3D to help user see an object at distance 0.33 m. The intermediate vision (IV) zone which may be viewing desktop display is producing zone corresponding to zero pitch of the optical power of 1D (distance of 1 m). Finally, the far vision zone (R) with optical power below 1D (from 1 m to infinity) can be found above IV zone.

The NV zone is illustrated to be slightly right from the middle. This is due to a rotation of the eyes in a rotation direction to the nose of the user when reading (convergence). FIG. 5 thus illustrates a right eye spectacle's lens customization for a user with presbyopia. The zones can be customized to the user's needs. As can be seen from FIG. 5, the optical powers may be distributed in a non-uniform manner respectively, whereby the zones' transitions may be smooth as well.

Consequently, an optimised lens power mapping based on personal visual behaviour may be provided.

More details and aspects are mentioned in connection with the embodiments described above or below. The embodiment shown in FIG. 5 may comprise one or more optional additional features corresponding to one or more aspects mentioned in connection with the proposed concept or one or more embodiments described above (e.g. FIGS. 1-4) or below (e.g. FIGS. 6-8).

FIG. 6 schematically illustrates a possible implementation of a power distribution/profile of an optical aid as an example of progressive addition spectacles lens. The optical aid in FIG. 5 is a lens having a round shape, from which the lens for fitting in spectacles may be cut along the dashed line. Since the required power zone profile shown in FIG. 5 cannot be implemented with a lens, the customization step is required to find a feasible design which accounts for the optical restrictions of the spectacle lens and matches desired profile as close as possible. Modern progressive additional lenses feature blending regions (BR) which are not usable for the good vision due to high astigmatism. They are required to blend the optical powers of lenses for far and near visions. The optical power gradually changes from distance reference point (DRP) for far vision to the near reference point (NRP) for near vision along the progressive corridor. This progression is defined by power profile. Power profile along with other parameters can be optimised to fit the required distribution.

More details and aspects are mentioned in connection with the embodiments described above or below. The embodiment shown in FIG. 6 may comprise one or more optional additional features corresponding to one or more aspects mentioned in connection with the proposed concept or one or more embodiments described above (e.g. FIGS. 1-5) or below (e.g. FIGS. 7-8).

FIG. 7 schematically illustrates an example of a power profile implementing design fitting required power map from FIG. 5 with the progressive addition lens layout from FIG. 6. These measurements may correspond to the distance measurements in the sagittal plane in accordance with FIG. 3. Optical power in this case is calculated as a reciprocal of the distance to the object of visual task. The eye pitch angle is calculated from the gaze angle on the FIG. 3 and measured head angles. These measurements may be extended to different planes. In the particular example, pitch of angle smaller than −5 degrees implements far distance vision, starting from DRP.

At the pitch around 0 the power equals to 1D (distance of 1 m, corresponding to example of desktop display in FIG. 3). With further increase in pitch angle profile reaches NRP with power of +3D (0.33 m), corresponding to handheld media in FIG. 3.

More details and aspects are mentioned in connection with the embodiments described above or below. The embodiment shown in FIG. 7 may comprise one or more optional additional features corresponding to one or more aspects mentioned in connection with the proposed concept or one or more embodiments described above (e.g. FIGS. 1-6) or below (e.g. FIG. 8).

FIG. 8 schematically illustrates a projection of pupil diameters at an optical aid's plane. In particular, light intensity/luminance and/or light spectral content may be measured by the visual field sensor and converted into the pupil size of the user using empirical formulas and models. Thus, the optical aid can be designed for different light intensity exposures of the user as well. The eye is known to accommodate differently in different lightning conditions. For example, in particular dark settings eye accommodates only between 0.5 and 2 meters (2 to 0.5 D, correspondingly). The depth of focus (the range of optical powers which are imaged on retina with sufficient quality) is inversely proportional to the pupil diameter, which means that in highly illuminated settings, the pupil constricts and the range increases. The depth of focus changes from 0.1D to 0.5D. This can be taken into account in the design of optical aid. In the example of FIG. 8 the pupil is larger for the lower zones, which means that the depth of focus would be reduced in these zones. This may be used to define the accuracy requirements to the map of optical powers of the visual aid, like the one shown in FIG. 5. In this example, the design of optical aid should deliver the optical power in the lower zones (used for near vision in this example) with high accuracy. In this example the upper zones are typically used with the pupil size decreased and thus depth of focus is increased which leads to the higher tolerance to defocus in this area. Thus there is a higher flexibility for the selection of optical powers of far distances located in the upper zones in this particular case.

More details and aspects are mentioned in connection with the embodiments described above or below. The embodiment shown in FIG. 8 may comprise one or more optional additional features corresponding to one or more aspects mentioned in connection with the proposed concept or one or more embodiments described above (e.g. FIGS. 1-7).

The example of the spectacles plane in FIG. 6 illustrates the case when visual aid is decoupled from the eyes and thus movement of the eyes may be associated with changes in the optical power of visual aid.

Another example of visual aid may represent contact lenses, corneal implants and/or intraocular lenses, which are moving with the eye. In this case the projection surface is always aligned with the gaze and head orientation is irrelevant. Nevertheless, the method allows to map the objects in the peripheral vision to the projection surface. A flow chart as illustrated in FIG. 2 may represent various processes, operations or steps, which may, for instance, be substantially represented in computer readable medium and so executed by a computer or processor, whether or not such computer or processor is explicitly shown. Methods disclosed in the specification or in the claims may be implemented by a device having means for performing each of the respective acts of these methods.

It is to be understood that the disclosure of multiple acts, processes, operations, steps or functions disclosed in the specification or claims may not be construed as to be within the specific order, unless explicitly or implicitly stated otherwise, for instance for technical reasons. Therefore, the disclosure of multiple acts or functions will not limit these to a particular order unless such acts or functions are not interchangeable for technical reasons. Furthermore, in some examples a single act, function, process, operation or step may include or may be broken into multiple sub-acts, -functions, -processes, -operations or -steps, respectively. Such sub acts may be included and part of the disclosure of this single act unless explicitly excluded.

The aspects and features mentioned and described together with one or more of the previously detailed examples and figures, may as well be combined with one or more of the other examples in order to replace a like feature of the other example or in order to additionally introduce the feature to the other example.

Furthermore, the following claims are hereby incorporated into the detailed description, where each claim may stand on its own as a separate example. While each claim may stand on its own as a separate example, it is to be noted that—although a dependent claim may refer in the claims to a specific combination with one or more other claims—other examples may also include a combination of the dependent claim with the subject matter of each other dependent or independent claim. Such combinations are explicitly proposed herein unless it is stated that a specific combination is not intended. Furthermore, it is intended to include also features of a claim to any other independent claim even if this claim is not directly made dependent to the independent claim.

The invention claimed is:

1. A system for determining an optical parameter distribution at a projection surface, the system comprising:
   a visual field sensor configured to measure a visual field of a user related to a specific vision task and further configured to determine gaze directions of the user during the specific vision task; and
   a head orientation and/or position sensor configured to measure head orientation and/or position of the user in relation to the visual field during the specific vision task;
   wherein the system is configured to enable computation of the user's eye orientation in relation to the head of the user based on the gaze directions of the user and the head orientation and/or position of the user to determine an optical parameter distribution at a projection surface between the visual field and a retina of the user;
   wherein the optical parameter distribution on the projection surface is used for customization of an optical aid, and wherein the optical parameter is optical powers.

2. The system of claim 1, wherein the visual field sensor is configured to identify an object of the visual field of the user related to the specific vision task and configured to derive the gaze directions of the user related to the identified object of the visual field.

3. The system according to claim 1, wherein the system further comprises a context sensor configured to measure at least one parameter related to an activity of the user.

4. The system according to claim 1, further comprising a statistical classifier configured to identify the vision task and/or object of the visual field of the user from at least one of:
   the visual field sensor;
   the head orientation and/or position sensor; and
   the context sensor,
   where identification is at least in part performed automatically.

5. The system according to claim 1, further comprising:
   a memory unit configured to store the head orientation and/or position and the gaze directions both related to the specific vision task, wherein the stored head orientation and/or position and the stored gaze directions form the basis for determining the optical parameter distribution at the projection surface between the visual field and the retina of the user.

6. The system according to claim 5, wherein the processing unit is configured to determine the corresponding differences between the stored head orientation and/or position and the stored gaze directions and to determine the optical parameter distribution at the projection surface between the visual field and the retina of the user.

7. The system according to claim 1, further comprising:
a processing unit configured to determine the corresponding differences between the head orientation and/or position and the gaze directions and to determine the optical parameter distribution at the projection surface between the visual field and the retina of the user.

8. The system according to claim 1, wherein the system is or is arranged in a head mounted wearable adapted to be worn by the user.

9. The system according to claim 8, wherein the wearable is a single module comprising all the elements of the system.

10. The system according to claim 8, wherein coordinate systems of the respective head orientation and/or position sensor and the respective visual field sensor are aligned.

11. The system according to claim 1, wherein the visual field sensor and the head orientation and/or position sensor are separated from each other; and/or
wherein the projection surface is associated with and/or linked to an optical aid.

12. The system according to claim 1, wherein the optical parameter distribution on the projection surface is used for customization of an optical aid, wherein optical parameter being at least one of:

pupil diameters;
depths of focus;
spectral content of light;
angular distribution of light; and
polarization state of light.

13. A method for determining an optical parameter distribution at a projection surface, the method comprising:
measuring, by a visual field sensor, a visual field of a user related to a specific vision task;
determining, by the visual field sensor, a gaze directions of the user during the specific vision task;
measuring, by a head orientation and/or position sensor, head orientation and/or position of the user in relation to the visual field during the specific vision task; and
enabling computation of the user's eye orientation in relation to the head of the user based on the gaze directions of the user and the head orientation and/or position of the user to determine an optical parameter distribution at a projection surface between the visual field and a retina of the user;
wherein the optical parameter distribution on the projection surface is used for customization of an optical aid, and wherein the optical parameter is optical powers.

14. A computer program product comprising program code portions for carrying out a method according to claim 13 when the computer program product is executed on one or more processing units, wherein the computer program product is stored on one or more non-transitory computer readable storage media.

15. An optical aid, wherein the optical aid is adjustable based on a method according to claim 13 or using a system according to claim 1.

* * * * *